United States Patent
Bai et al.

(10) Patent No.: US 11,828,826 B2
(45) Date of Patent: Nov. 28, 2023

(54) ANALYSIS METHOD OF DYNAMIC CONTRAST-ENHANCED MRI

(71) Applicant: ZHEJIANG UNIVERSITY, Hangzhou (CN)

(72) Inventors: Ruiliang Bai, Hangzhou (CN); Zejun Wang, Hangzhou (CN); Guangxu Han, Hangzhou (CN)

(73) Assignee: ZHEJIANG UNIVERSITY, Hangzhou (CN)

(*) Notice: Subject to any disclaimer, the term of this patent is extended or adjusted under 35 U.S.C. 154(b) by 393 days.

(21) Appl. No.: 17/421,012

(22) PCT Filed: Jul. 8, 2020

(86) PCT No.: PCT/CN2020/100740
§ 371 (c)(1),
(2) Date: Jul. 6, 2021

(87) PCT Pub. No.: WO2021/004465
PCT Pub. Date: Jan. 14, 2021

(65) Prior Publication Data
US 2022/0018924 A1 Jan. 20, 2022

(30) Foreign Application Priority Data
Jul. 10, 2019 (CN) .......................... 201910621579.6

(51) Int. Cl.
*G01R 33/00* (2006.01)
*G01R 33/563* (2006.01)
*G01R 33/56* (2006.01)

(52) U.S. Cl.
CPC ... *G01R 33/56308* (2013.01); *G01R 33/5601* (2013.01)

(58) Field of Classification Search
CPC .............................................. G01R 33/56308
See application file for complete search history.

(56) References Cited

U.S. PATENT DOCUMENTS

2010/0253342 A1  10/2010  Kimura

FOREIGN PATENT DOCUMENTS

| CN | 101912262 | 12/2010 |
|---|---|---|
| CN | 103027682 | 4/2013 |

(Continued)

*Primary Examiner* — Joseph M Santos Rodriguez
(74) *Attorney, Agent, or Firm* — Jiwen Chen; Joywin IP Law PLLC

(57) ABSTRACT

The present invention discloses an analysis method for dynamic contrast-enhanced magnetic resonance image. Firstly, the time-series signal of vascular contrast agent concentration, AIF, of biological individual is obtained from DCE-MRI time-series data. Secondly, perform the nonlinear least sum of square fitting by using the full Shutter-Speed model ($SSM_{full}$) and the simplified vascular Shutter-Speed model ($SSM_{vas}$) on the DCE-MRI time-series signal of each pixel, and the fitting results of DCE-MRI time-series signal are obtained. Thirdly, the corrected Akaike Information Criterion ($AIC_C$) score is used to comparing the DCE-MRI time-series signal fitting results to select the optimal model. If the optimal model is $SSM_{full}$, distribution maps of five physiological parameters. $K^{trans}$, $p_b$, $p_o$, $k_{bo}$, and $k_{io}$, are produced after fitting; if the optimal model is $SSM_{vas}$, distribution maps of three physiological parameters, $K^{trans}$, $p_b$, and $k_{bo}$, are produced after fitting. Finally, perform error analysis on the $k_{io}$ and $k_{bo}$, resulting the final distribution maps of $k_{io}$ and $k_{bo}$ along with distribution maps of parameters $K^{trans}$, $p_b$, $p_o$. This method can improve the estimation accuracy of $K^{trans}$, $p_b$, $p_o$, $k_{bo}$ and $k_{io}$.

8 Claims, 9 Drawing Sheets

(56) References Cited

FOREIGN PATENT DOCUMENTS

| CN | 103076583 | 5/2013 |
|---|---|---|
| CN | 103514607 | 1/2014 |

ANALYSIS METHOD OF DYNAMIC CONTRAST-ENHANCED MRI

This is a U.S. national stage application of PCT Application No. PCT/CN2020/100740 under 35 U.S.C. 371, filed Jul. 8, 2020 in Chinese, claiming priority to Chinese Patent Applications No. 201910621579.6, filed Jul. 10, 2019, all of which are hereby incorporated by reference.

TECHNICAL FIELD

The present invention belongs to the field of imaging technology, in particular to an analysis method of dynamic contrast-enhanced magnetic resonance images.

BACKGROUND TECHNOLOGY

DCE-MRI (dynamic contrast-enhanced magnetic resonance imaging) uses fast MRI sequence to continuously collect images before, during and after intravenous injection of contrast agent to show the information that contrast agent enters target organs or blood vessels, passes through capillaries and is finally cleared. Conventional contrast-enhanced MRI can only diagnose by morphological features of lesions, and it can only reflect the enhancement characteristics of a certain or some fixed time points, and the result analysis depends on the doctor's experience. DCE-MRI can produce continuous and dynamic images by multi-phase scanning, which can reflect the enhancement characteristics of lesions more objectively, and have more abundant and comprehensive information on the pathophysiological characteristics of the displayed areas. In this sense, DCE-MRI, like other functional imaging techniques, can identify the pathophysiological characteristics of lesions in addition to displaying their anatomical structures.

At present, there are mainly two methods for DCE-MRI data analysis: semi quantitative analysis and quantitative analysis. Semi quantitative analysis is based on multiple metrics obtained from the signal intensity time-dependent curve to describe the characteristics of tissue enhancement, and does not involve the application of pharmacokinetic models. Quantitative analysis can calculate the concentration of contrast agent in the region of interest, and then improve the comparability of different research results. Quantitative analysis can also fit the pharmacokinetic model to analyze and calculate the signal intensity time-dependent curve, and derive a series of quantitative parameters for evaluation. After decades of development, the current pharmacokinetic models have many choices from single parameter to multi parameters, for example, four-parameter models can be divided into plasma model interstitial model, exchange model, and boundary stage model. The typical representatives of the three-parameter models are the extended Tofts model and two-parameter model includes single chamber model and Patlak model. The SSM model mentioned in the present invention is also one of the pharmacokinetic models for quantitative analysis of DCE-MRI.

In recent years, DCE-MRI analysis method based on transmembrane water exchange (TWE) has been proposed and proved to be a novel, high-resolution, non-invasive method of describing cell metabolic activity (Springer et al., 2014; Rooney et al., 2015; Springer, 2018). The results show that the transmembrane water exchange in biological tissues is determined mainly by the active pathway, which is a metabolism-dependent process mainly driven by Na-K-ATPase (NKA) pump (Springer, 2018). The transmembrane water exchange rate constant of normal brain tissue can reach $2\ s^{-1}$, and the metabolic driving component can reach 70% (Bai et al., 2018b). As long as enough contrast agent (CA) penetrates into the extravascular-extracellular space, the metabolism image based on TWE can be realized by analyzing the shutter speed model (SSM) of DCE-MRI time-series data (Springer, 2018). The SSM analysis based on DCE-MRI has the advantages of submillimeter spatial resolution, low cost and convenient for clinical use. Recently, SSM analysis based on DCE-MRI revealed intratumoral heterogeneity, showing the possibility of being a potential biomarker for evaluating chemotherapy outcomes (Springer et al., 2014).

In the conventional SSM analysis of DCE-MRI data, in order to reduce the model fitting parameters, a single SSM sub model is often selected for a certain disease. For example, in muscle, (Landis et al., 1999), breast cancer (Huang et al., 2011; Springer et al., 2014), prostate cancer (Li et al., 2012), esophageal cancer (Bai et al., 2018a), head and neck cancer (Chawla et al., 2018), it is often considered that there is enough contrast agent outflow, and the SSM submodel without vascular factors is used for analysis. However, in biological tissues, especially in brain lesions, biological tissues often show complexity, and a single SSM submodel cannot meet the accurate analysis of all pixels. For example, in normal brain tissue, because of the existence of blood-brain barrier (BBB), contrast media cannot leak from blood vessels quickly, so it is necessary to establish a new SSM sub model. However, in brain tumors, due to the increase of vascular density and permeability, there may be a large number of contrast media leakage, so $SSM_{full}$ model is more suitable.

SUMMARY OF THE INVENTION

The purpose of the present invention is to provide an analysis method of dynamic contrast-enhanced magnetic resonance image, in other words, a general analysis method of the shutter speed model (SSM) of dynamic contrast-enhanced magnetic resonance image, which can automatically match the best SSM model for each pixel, so as to improve the estimation accuracy of the five physiological parameters: contrast agent volume transfer constant between blood plasma and extravascular-extracellular space ($K^{trans}$), intravascular water mole fractions ($p_b$), extravascular-extracellular water mole fractions ($p_o$), vascular water efflux rate constant ($k_{bo}$) and the cellular water efflux rate constant ($k_{io}$).

The present invention provides the following technical solutions:

An analysis method of dynamic contrast-enhanced magnetic resonance image, the analysis method includes the following steps:

(1) Obtaining the time-series signal of vascular contrast agent concentration, AIF, of biological individual in DCE-MRI time-series data.

(2) According to the time-series signal of vascular contrast agent concentration in step (1), the DCE-MRI time-series signal of each pixel is fitted with the nonlinear least square algorithm and two SSM models including the full shutter speed model ($SSM_{full}$) and the simplified vascular shutter speed model ($SSM_{vas}$). The DCE-MRI signal fitting results of $SSM_{full}$ and $SSM_{vas}$ of each pixel are then obtained, respectively.

(3) The DCE-MRI signal fitting results of $SSM_{full}$ and $SSM_{vas}$ of each pixel is scored and compared using the corrected Akaike Information Criterion. According to the corrected Akaike Information Criterion scores of $SSM_{full}$ model and $SSM_{vas}$ model of each pixel, the optimal model is selected from $SSM_{full}$ and $SSM_{vas}$.

(4) According to the optimal model selected in step (3), when the optimal model is $SSM_{full}$, the distribution maps of five physiological parameters are generated after fitting. The five physiological parameters include $K^{trans}$, $p_b$, $p_o$, $k_{bo}$ and $k_{io}$; when the optimal model is $SSM_{vas}$, because $p_o$ and $k_{io}$ are not as the estimated parameters, the distribution maps of three physiological parameters are generated after fitting and the three physiological parameters are $K^{trans}$, $p_b$ and $k_{bo}$.

(5) The error analysis of $k_{io}$ and $k_{bo}$ in step (4) is carried out. Only pixel results with 95% confidence interval in [0 s$^{-1}$ 20 s$^{-1}$] or the lower limit of 95% confidence interval bigger than 5 s$^{-1}$ are retained to generate the final distribution map of $k_{io}$ and $k_{bo}$, along with the distribution map of $K^{trans}$, $p_b$, $p_o$.

The $SSM_{full}$ in the step (2) is the complete DCE-MRI shutter speed model (full shutter speed model). The specific method of $SSM_{full}$ is as follows. $SSM_{full}$ divides water molecules into three compartments (blood vessel (b), interstitial (o) and intracellular space (i)). In other words, water molecules are in three physical spaces of vascular space, extravascular-extracellular space and intercellular space, and are in two exchange process, including water molecule exchange between vascular and extravascular-extracellular space and between intercellular space and extravascular-extracellular space. It is assumed that there is no exchange of water molecules between vascular and intracellular spaces. In this method, the longitudinal relaxation time (T1) contrast agent, such as Magnevist, ProHance, etc., is used. The concentration of contrast agent in the interstitial space $[CA_o]$ (T) was determined by the Kety Schmidt rate law, $$\frac{[CA_o](T) = K^{trans} v_o^{-1} \int_o^T [CA_p](t) \exp(-K^{trans} v_o^{-1}(T-t))}{dt} \quad (1)$$

Among them, $v_o$ is the volume fraction of interstitial space, and is linearly proportional to $p_o(v_o=p_o f_w)$, $[CA_p]$ is the concentration of CA in plasma, T is the measurement time, t is the time to carry out, $f_w$ is t the tissue volume fraction accessible to mobile aqueous solutes (here the fixed value is 0.80).

The $SSM_{full}$ in step (2) is composed of five independent physiological parameters: $K^{trans}$, $p_b$, $p_o$, $k_{bo}$ and $k_{io}$ where $K^{trans}$ is obtained by the CA extravasation rate constant $k_{pe}$ and plasma volume fraction $v_p$ ($K^{trans}=k_{pe}*v_p$, $v_p=v_b(1-h)=p_b f_w(1-h)$, $v_b$ is the fraction of blood volume, h is the microvascular hematocrit (=0.42), $f_w$ is the tissue volume fraction accessible to mobile aqueous solutes (=0.80). The mole fraction of intracellular water $p_i$ was obtained by the relationship between $p_o+p_i+p_b=1$. In the $SSM_{full}$, the fast exchange limit of water exchange between blood plasma and blood cells is assumed.

The $SSM_{full}$ in step (2) assumes that the system is in equilibrium or steady state (homeostasis), The exchange process of water molecules in any two physical spaces satisfies the principle of microscopic reversibility (detailed equilibrium):

$$k_{io}/k_{oi} = p_o/p_i \quad (2)$$

$$k_{bo}/k_{ob} = p_o/p_b \quad (3)$$

The $SSM_{full}$ in step (2) comprehensively considers the water longitudinal relaxation and exchange into Bloch equation, and the specific form can be expressed as follows:

$$\frac{dM}{dt} = XM + C \quad (4)$$

Among them, the longitudinal magnetization vector and relaxation rate vector are $M=(M_b, M_o, M_i)$ and $C=(M_{b0}R_{1b}, M_{o0}R_{1o}, M_{i0}R_{1i})$, respectively. The subscript "0" represents the equilibrium state, and $R_{1b}$, $R_{1o}$ and $R_{1i}$ represent the longitudinal relaxation rate constants of blood, interstitial and intracellular water without exchange. $R_{1b}$ and $R_{1o}$ are linearly related to the contrast agent concentration [CA] in the corresponding space, that is, $R_1=R_{1,0}+r_1[CA]$, $r_1$ is the longitudinal relaxation rate of CA, and $R_1$ is $R_{1b}$ or $R_{1o}$. In the present invention, the exchange matrix X is as follows:

$$X = \begin{pmatrix} -(R_{1b}+k_{bo}) & k_{ob} & 0 \\ k_{bo} & -(R_{1o}+k_{ob}+k_{oi}) & k_{io} \\ 0 & k_{oi} & -(R_{1i}+k_{io}) \end{pmatrix} \quad (5)$$

For DCE-MRI based on Gradient Recalled Echo (GRE) the time-series signal strength S follows the MR steady-state hypothesis, which is expressed as follows:

$$S = 1_{1\times 3} M = 1_{1\times 3} [I - e^{TR \cdot X} \cos(\alpha)]^{-1} (I - e^{TR \cdot X}) M_0 \sin(\alpha) \quad (6)$$

TR and $\alpha$ are the repetition time and flip angle of GRE sequence, respectively.

$SSM_{vas}$ in step (2) is a simplified model of $SSM_{full}$. On the basis of $SSM_{full}$, $SSM_{vas}$ further assumes that the influence of the water exchange between extravascular-extracellular and intracellular spaces on the time-series signal of DCE-MRI is ignored, that is, the basic assumption of $SSM_{vas}$ is that water molecules are in three physical spaces of blood vessel, extravascular-extracellular space and intercellular space, and there is water molecule exchange between vascular and extravascular-extracellular spaces, but there is no water molecule exchange between vascular and intracellular spaces, and the effect of transmembrane water exchange between intracellular and extravascular-extracellular spaces and the intracellular water mole fraction on magnetic resonance signal can be ignored. $p_o$ and $k_{io}$ are not fitting parameters and fixed at 0.20 and 1000 s$^{-1}$, respectively. Therefore, there are three pharmacokinetic or physiological parameters to be estimated in $SSM_{vas}$, which are $K^{trans}$, $p_b$ and $k_{bo}$.

In step (3), if the difference between the corrected Akaike Information Criterion scores of $SSM_{full}$ and $SSM_{vas}$ in a pixel is no more than −10, the optimal model for this pixel is $SSM_{full}$, and if the difference is more than −10, the optimal model is $SSM_{vas}$.

The calculation formula of the corrected Akaike Information Criterion ($AIC_c$) score is as follows:

$$AIC_c = -2\log\mathcal{L} + 2K \frac{N}{N-K-1} \quad (7)$$

Among them, K is the number of independent parameters of the fitting model and equal to 4 and 6 for $SSM_{vas}$ and $SSM_{full}$, respectively, N is the number of measurement points in DCE-MRI data, and log L is the maximum logarithmic likelihood probability.

In step (5), the error analysis is mainly used to determine the 95% confidence interval for the parameters of vascular water efflux rate constant ($k_{bo}$) and the cellular water efflux rate constant ($k_{io}$). The 95% confidence interval of $k_{bo}$ or $k_{io}$ in the error analysis is determined as follows: fix the value of $k_{bo}$ or $k_{io}$ and fit all the remaining parameters through the nonlinear least square sum of squares, and then change the value of $k_{bo}$ or $k_{io}$ within the interval of [0 s$^{-1}$ 20 s$^{-1}$] in small steps, and repeat the fitting until:

$$\chi^2 \geq \chi_0^2 \left[ 1 + \frac{K}{N-K} F(K, N-K, 0.95) \right] \quad (8)$$

Among them, $\chi^2$ is the reduced chi-squared value from the fitting with the $k_{bo}$ or $k_{io}$ fixed at a certain value, $\chi_0^2$ is the reduced chi-squared value with all parameters optimized, F is the F distribution function, K is the number of independent parameters in the fitting model, and N is the number of measurement points in the DCE-MRI data.

The analysis method (automatic shutter speed analysis method) provided by the present invention provides two SSM models (SSM full model (SSM$_{full}$) and simplified SSM model SSM$_{vas}$ without consideration of water molecule exchange across cell membrane) that can cover different physiological conditions of tissues. For the first time, the best SSM of each pixel is automatically matched by using the corrected Akaike Information Criterion method, so as to improve the estimation accuracy of the following five physiological parameters of DCE: contrast agent volume transfer constant between blood plasma and extravascular-extracellular space ($K^{trans}$) intravascular water mole fractions ($p_b$), extravascular-extracellular water mole fractions ($p_o$), vascular water efflux rate constant ($k_{bo}$), and the cellular water efflux rate constant ($k_{io}$). The present invention mainly aims at the complex situation of vascular permeability in biological tissues, such as glioblastoma. By providing two kinds of SSM models covering different physiological situations and providing automatic screening methods of the two models, the shutter speed model analysis of biological tissues with spatial heterogeneity is realized. At the same time, the present invention overcomes the potential bias of $k_{io}$ estimation due to insufficient leakage of contrast agent by error analysis method.

SPECIFIC DESCRIPTION OF THE EMBODIMENTS

The present invention is further described in detail below in conjunction with the accompanying figures and embodiments (e.g., head imaging).

Figure 1:
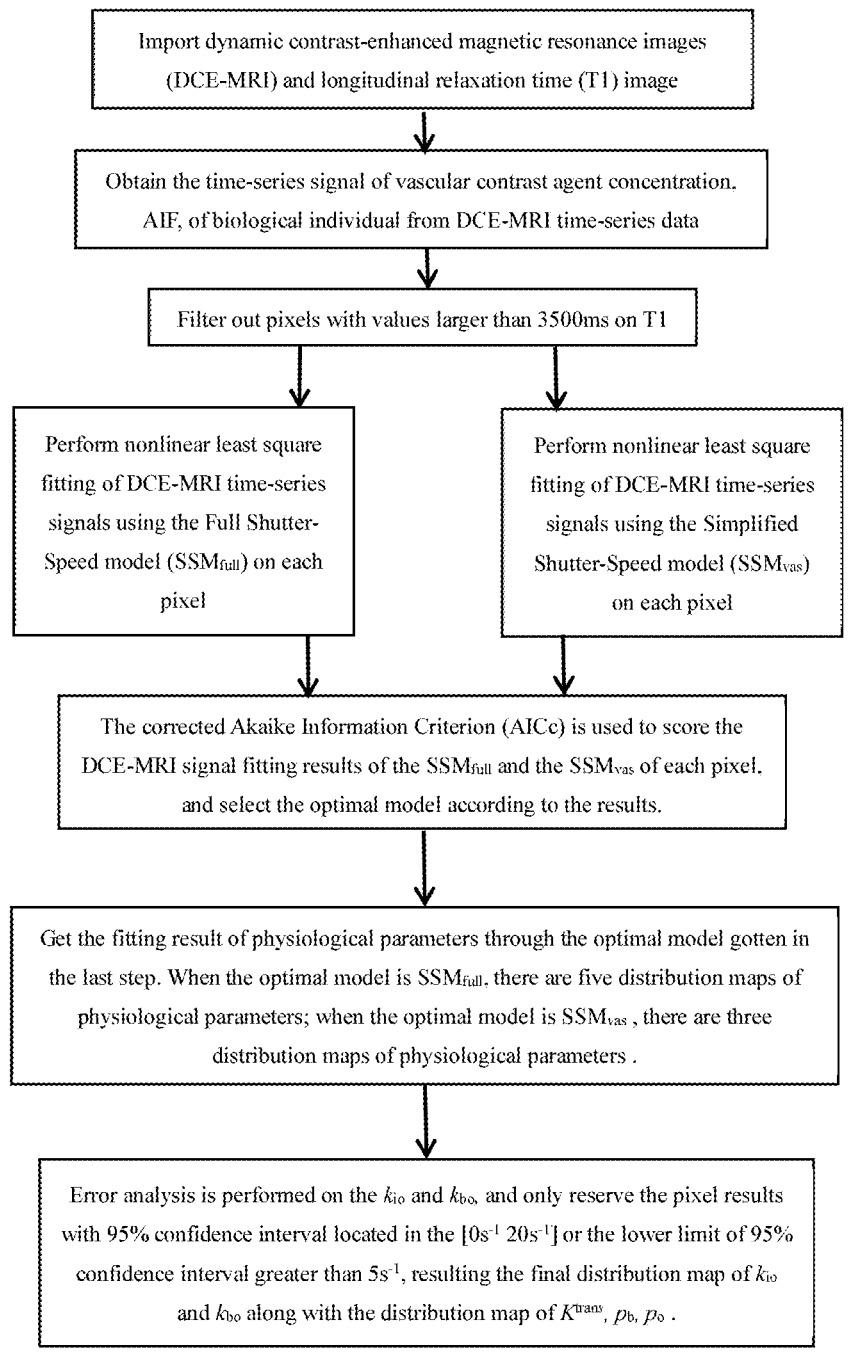
FIG. 1 shows the calculation flow chart of the general shutter speed model analysis method of dynamic contrast-enhanced magnetic resonance image provided by the present invention.

1. As shown in FIG. 1, dynamic contrast-enhanced MRI and T1 images are imported at first.

2. As shown in FIG. 1, according to the imported image, time-series signal of vascular contrast agent concentration AIF of the biological individual is obtained.

Figure 6:
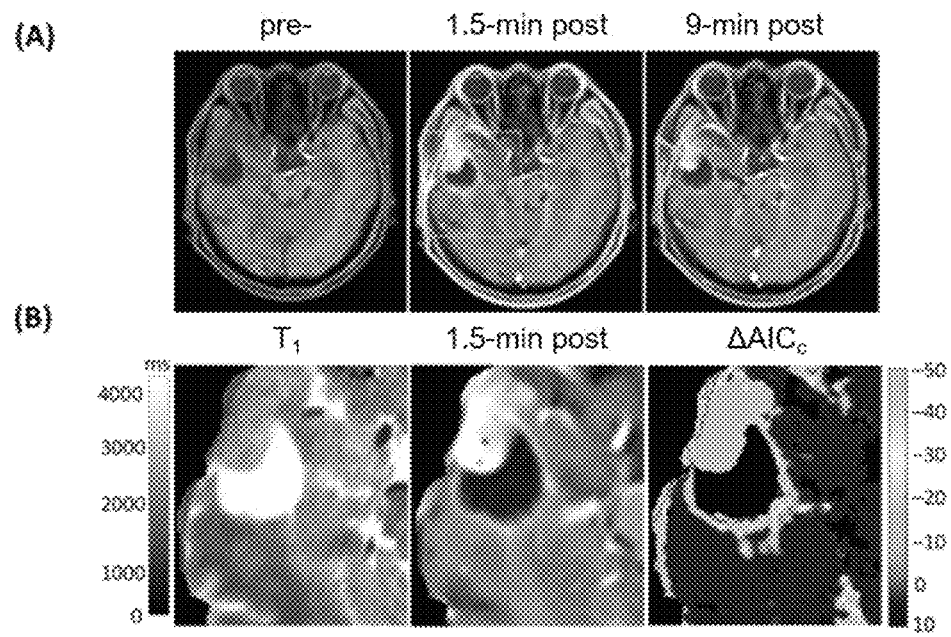
FIG. 6 shows the MRI data of glioma subjects.

3. As shown in FIG. 1, pixels with longitudinal relaxation time T1 larger than 3500 ms in the image are filtered out, because most of them are cerebrospinal fluid, there pixels are not analyzed. As shown in FIG. 6, the data from the T1<3500 ms pixels are analyzed in this embodiment. It is generally believed that the pixels with T1 greater than 3500 ms are mainly cerebrospinal fluid in 3T MRI brain imaging.

4. As shown in FIG. 1, the nonlinear least square sum fitting of SSM$_{full}$ and SSM$_{vas}$ is performed on each DCE-MRI time-series signals pixel, and the DCE-MRI signal fitting results of SSM$_{full}$ and SSM$_{vas}$ of each pixel are obtained respectively.

Figure 5:
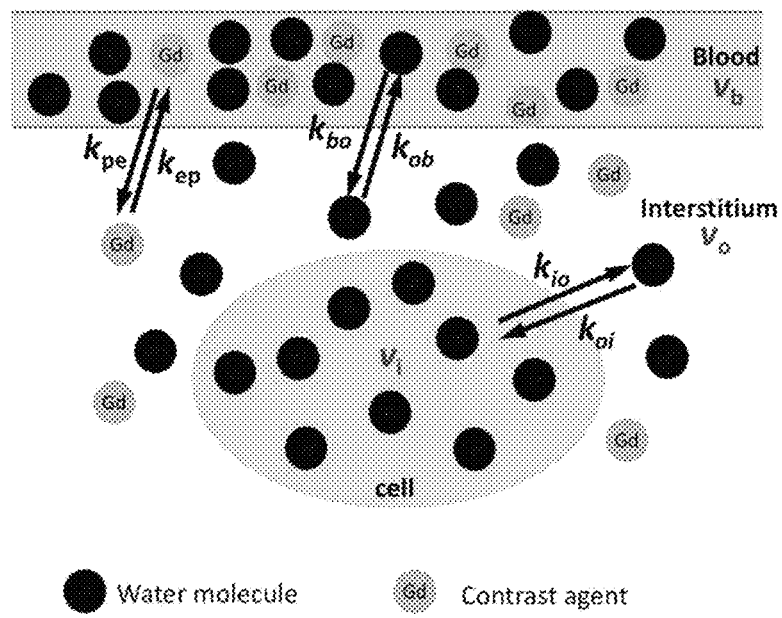
FIG. 5 is a schematic diagram of the shutter speed model.

As shown in FIG. 5, SSM$_{full}$ is a comprehensive three-point two exchange model, and three-point (physical space) includes water molecules in blood vessels, extravascular-extracellular space and intercellular space. Two exchange refers to water molecule exchange between blood and extravascular-extracellular space and water molecule exchange between intercellular space and extravascular-extracellular space. In the present invention, it is considered that the direct exchange of water molecules between blood and cells can be ignored in SSM$_{full}$. SSM$_{vas}$ is a simplified three-point two-exchange model. It is considered that the effect of water exchange between intercellular space and extravascular-extracellular space and extravascular-extracellular water molar fraction to DCE-MRI signal can be ignored.

Figure 2:
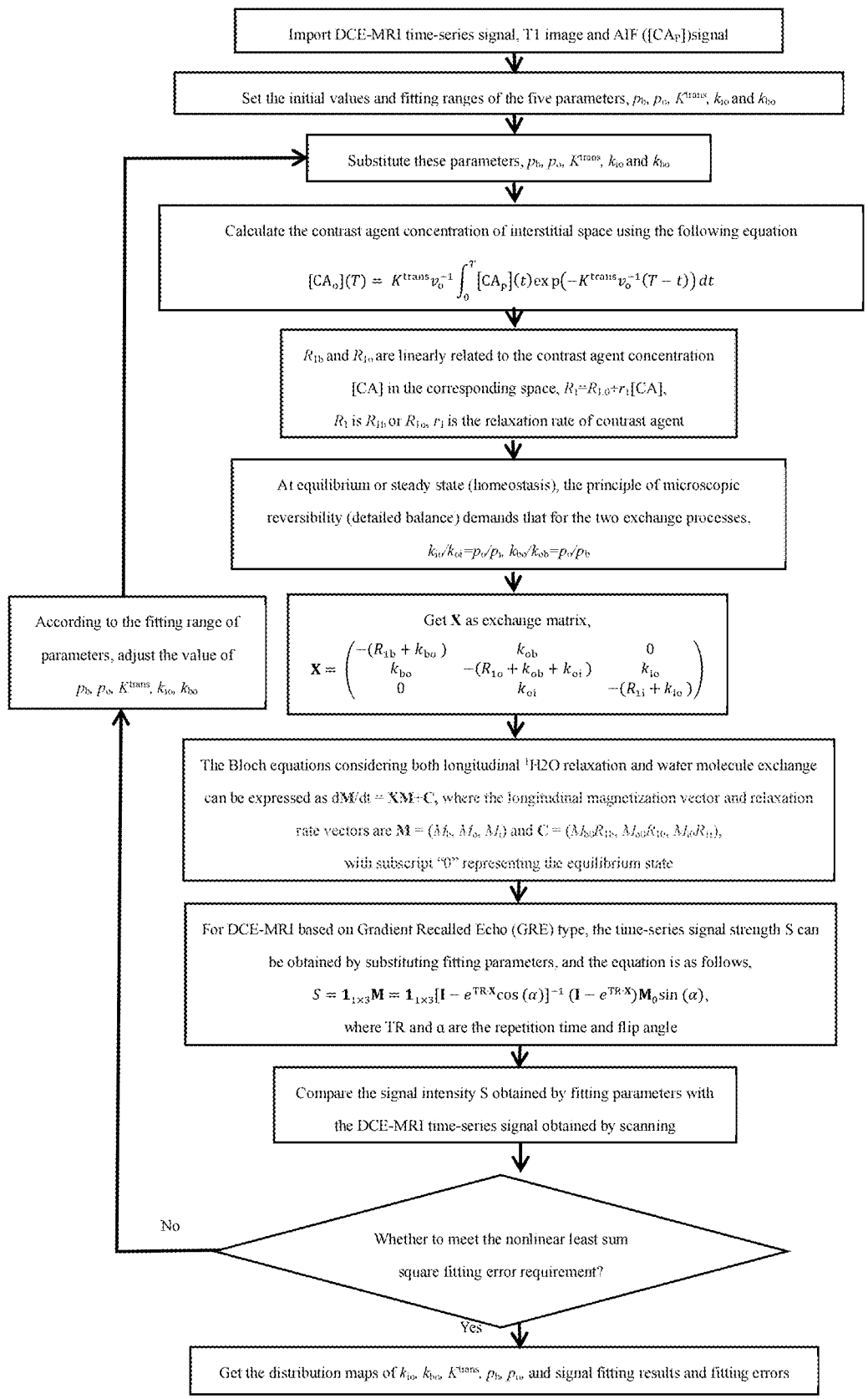
FIG. 2 shows the calculation flow chart of the full shutter speed model (SSM$_{full}$).

(4-1) As shown in FIG. 2, the SSM$_{full}$ model is used to fit the DCE-MRI time-series signals of each pixel respectively, and the specific process of obtaining the DCE-MRI signal fitting results of SSM$_{full}$ of each pixel point is as follows:

(4-1-1) in the SSM$_{full}$, DCE-MRI time-series signal, T1 image and AIF (namely [CA$_p$]) signal is imported at first.

(4-1-2) SSM$_{full}$ sets the initial values and ranges of the five fitting parameters, $p_b$, $p_o$, $K^{trans}$, $k_{io}$, $k_{bo}$. In this embodiment, the initial values of the five parameters are 0.02, 0.2, 0.01 min$^{-1}$, 3 s$^{-1}$, 3 s$^{-1}$, and the fitting ranges are 0.001~0.3, 0.01~0.65, 10$^{-5}$~1 min$^{-1}$, 0~20 s$^{-1}$, 0~20 s$^{-1}$, respectively.

(4-1-3) Substitute the five parameters $p_b$, $p_o$, $K^{trans}$, $k_{io}$, $k_{bo}$.

(4-1-4) Calculate the contrast agent concentration in interstitial space according to the following formula, $$[CA_o](T) = K^{trans} v_o^{-1} \int_0^T [CA_p](t) \exp(-K^{trans} v_o^{-1}(T-t)) dt$$

where $v_o$ is the volume fraction of interstitial space and is linearly proportional to $p_o$ ($v_o = p_o f_w$), [CA$_p$] is the concentration of CA in plasma, T is the measurement time, t is the time to proceed.

(4-1-5) $R_{1b}$ and $R_{1o}$ are obtained from the contrast agent concentration [CA], assuming that they were linearly related to the contrast agent concentration, that is, $R_1 = R_{1,0} + r_1[CA]$, $R_1$ is $R_{1b}$ or $R_{1o}$, and $r_1$ is the relaxation rate of contrast agent.

(4-1-6) $k_{oi}$ and $k_{ob}$ are obtained by proportional relation, because in equilibrium or steady state (homeostasis), the two water exchange processes satisfy the principle of microscopic reversibility, that is, $k_{io}/k_{oi}=p_o/p_i$, $k_{bo}/k_{ob}=p_o/p_b$, where $p_i=1-p_b-p_o$.

(4-1-7) it can be obtained that the exchange matrix is X, and X is shown in the following formula, $$X = \begin{pmatrix} -(R_{1b}+k_{bo}) & k_{ob} & 0 \\ k_{bo} & -(R_{1o}+k_{ob}+k_{oi}) & k_{io} \\ 0 & k_{oi} & -(R_{1i}+k_{io}) \end{pmatrix}$$

(4-1-8) The Bloch equation considering the longitudinal $^1$H2O relaxation and water molecule exchange can be expressed as dM/dt=XM+C, where the longitudinal magnetization vector and relaxation rate vector are M=($M_b$, $M_o$, $M_i$) and C=($M_{b0}R_{1b}$, $M_{o0}R_{1o}$, $M_{i0}R_{1i}$), respectively. The subscript "0" represents the equilibrium state.

(4-1-9) For DCE-MRI based on Gradient Recalled Echo (GRE) type, the time-series signal strength S can be obtained by substituting parameters, and the formula is as follows:

$$S = 1_{1\times3}M = 1_{1\times3}[I-e^{TR\cdot X}\cos(\alpha)]^{-1}(I-e^{TR\cdot X})M_0\sin(\alpha)$$

TR and α are the reputation time and flip angle of GRE sequence, respectively (4-1-10) Compare the fitted time-series signal strength S obtained by substituting the parameters with the scanned DCE-MRI time-series signal.

(4-1-11) Judge whether the fitting results meet the fitting error requirements of nonlinear least square sum algorithm.

(4-1-12) If step (4-1-11) does not meet the requirements, adjust the substitution values of five parameters $p_b$, $p_o$, $K^{trans}$, $k_{io}$, $k_{bo}$ according to the parameter fitting range and nonlinear least square algorithm iteration, and start from step (4-1-3) again until the requirements of step (4-1-11) are met.

(4-1-13) If step (4-1-11) is satisfied, the $p_b$, $p_o$, $K^{trans}$, $k_{io}$, $k_{bo}$ of SSM$_{full}$ fitting can be obtained, and then $p_b$, $p_o$, $K^{trans}$, $k_{io}$, $k_{bo}$ parameter distributions, signal fitting results and fitting error of all pixels fitted by SSM$_{full}$ can be obtained.

Figure 3:
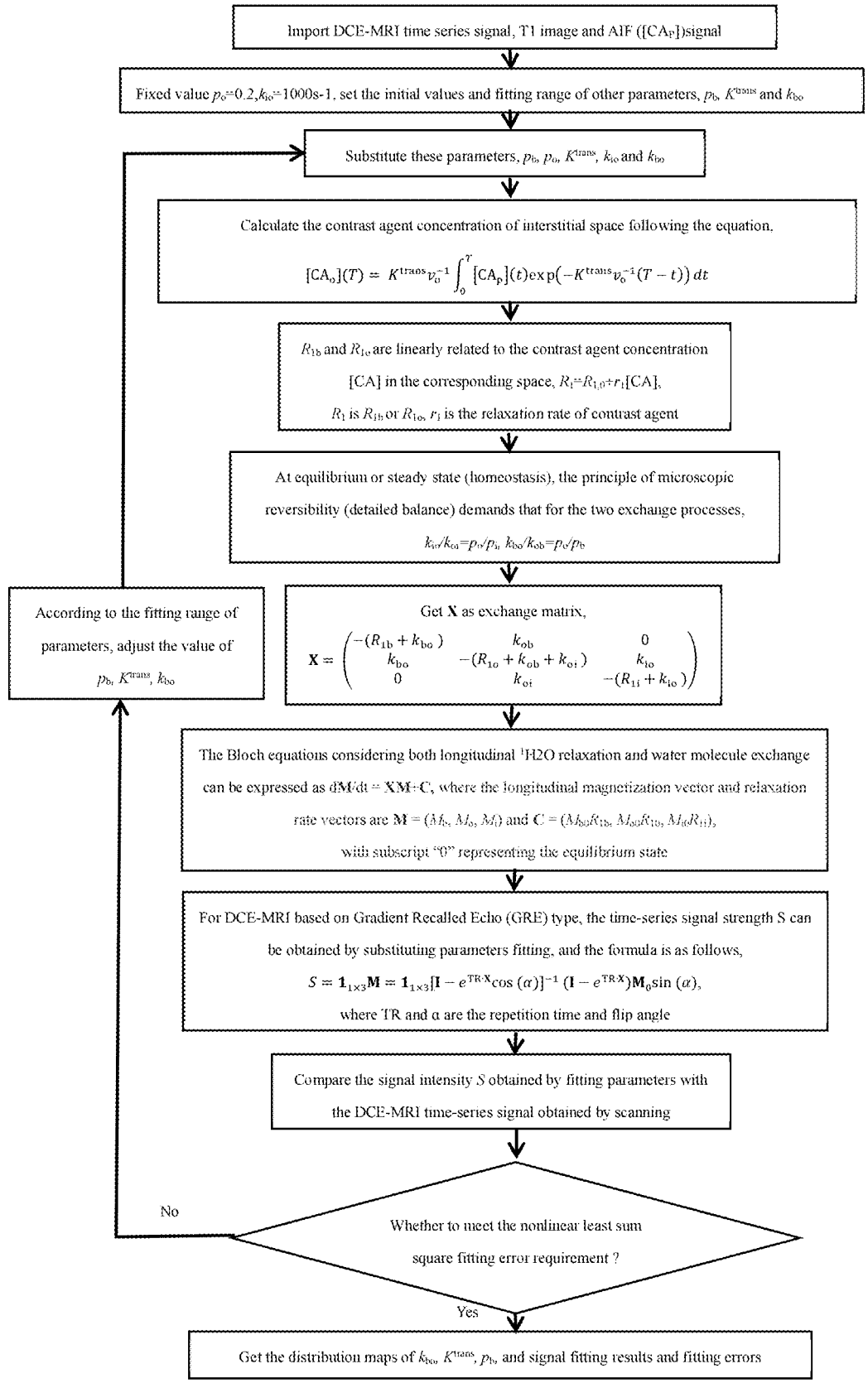
FIG. 3 shows the flow chart of simplified vascular shutter speed model (SSM$_{vas}$).

(4-2) As shown in FIG. 3, the SSM$_{vas}$ is used to fit the DCE-MRI time-series signals of each pixel respectively for nonlinear least square sum fitting. The specific process of obtaining the fitting results of DCE-MRI signals of SSM$_{vas}$ of each pixel is as follows:

(4-2-1) Firstly, DCE-MRI time-series signal, T1 signal and AIF (i.e. [CA$_p$]) signal were imported into SSM$_{vas}$.

(4-2-2) Fix $p_o$=0.2 and $k_{io}$=1000 s$^{-1}$ in SSM$_{vas}$, and set the initial values and fitting ranges of three parameters $p_b$, K$^{trans}$ and $k_{bo}$. In this embodiment, the initial values of the three parameters and the fitting range and steps (4-1-2) are the same.

(4-2-3) Substitute the five parameters $p_b$, $p_o$, K$^{trans}$, $k_{io}$, $k_{bo}$.

(4-2-4) repeat steps (4-1-3) to (4-1-9)

(4-2-5) The parameters are substituted into the fitted signal strength S and compare S with the scanned DCE-MRI time-series signal.

(4-2-6) Judge whether the fitting results meet the fitting error requirements of nonlinear least square sum algorithm.

(4-2-7) if step (4-2-6) is not satisfied, adjust the substitution values of $p_b$, K$^{trans}$ and $k_{bo}$ according to the parameters fitting range and nonlinear least squares sum algorithm iteration, and start from step (4-2-3) again until the requirements of step (4-2-6) are met. If step (4-2-6) is satisfied, the $p_b$, K$^{trans}$ and $k_{bo}$ of SSM$_{vas}$ fitting can be obtained, and then the $p_b$, K$^{trans}$ and $k_{bo}$ parameter distributions of all pixels fitted by SSM$_{vas}$, as well as signal fitting results and fitting errors, can be obtained.

5. As shown in FIG. 1, after the SSM$_{full}$ and SSM$_{vas}$ fitting are completed, the corrected Akaike Information Criterion is used to score the two submodels of each pixel, and the optimal model is selected by scoring.

Figure 4:
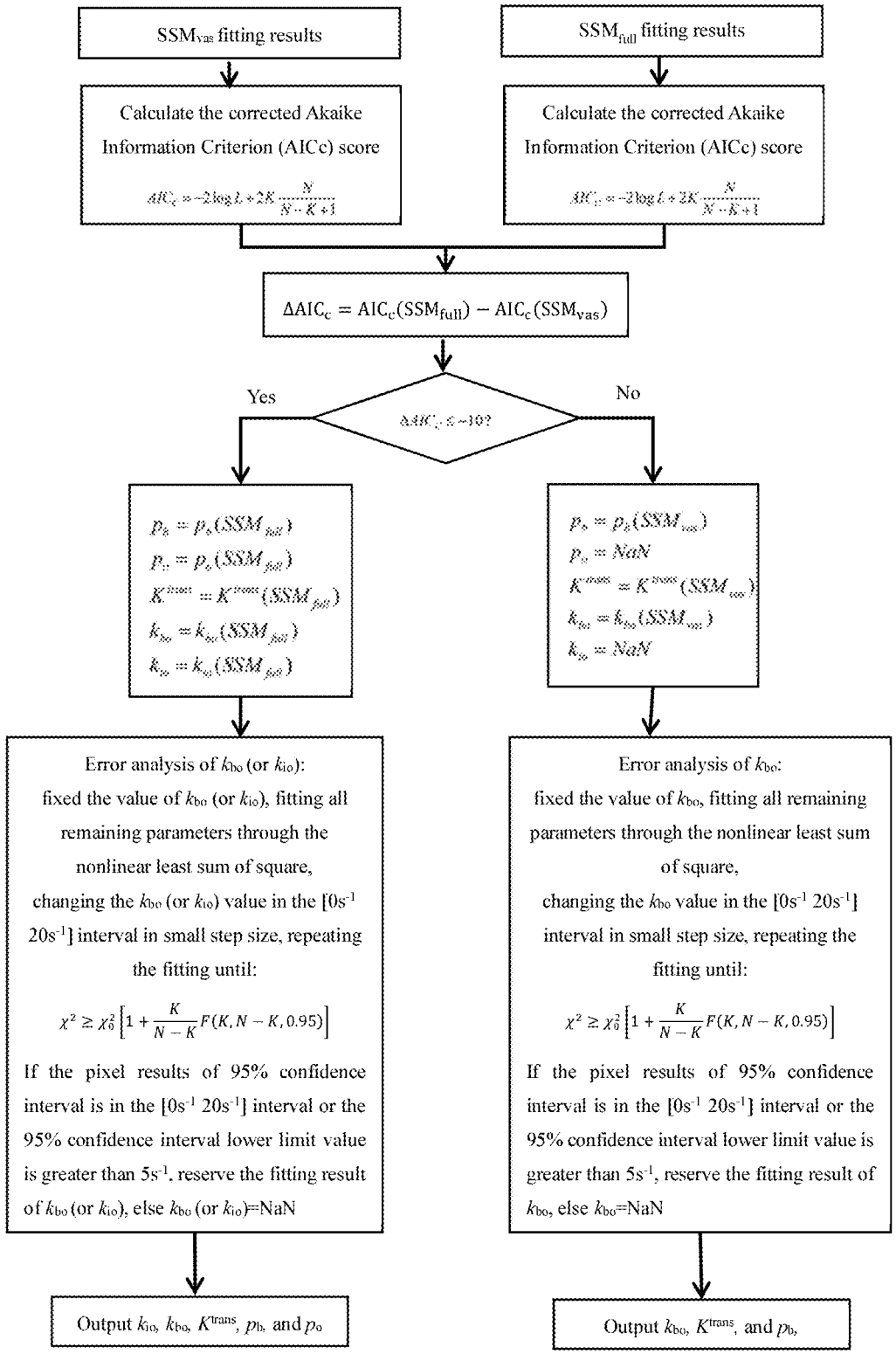
FIG. 4 shows the calculation flow chart of the error analysis of SSM$_{full}$ and SSM$_{vas}$.

6. As shown in FIG. 4, DCE-MRI signal fitting results of SSM$_{full}$ and SSM$_{vas}$ of each pixel are scored and compared by using the corrected Akaike Information Criterion of SSM$_{full}$ and SSM$_{vas}$ of each pixel, and the optimal model is selected from SSM$_{full}$ and SSM$_{vas}$ according to the corrected Akaike Information Criterion score of SSM$_{full}$ and SSM$_{vas}$ of each pixel.

(6-1) In the error analysis after fitting, the fitting results of SSM$_{full}$ and SSM$_{vas}$ are imported firstly.

(6-2) The corrected Akaike Information Criterion scores of SSM$_{full}$ and SSM$_{vas}$ are calculated respectively. Among them, the calculation formula of corrected Akaike Information Criterion score is as follows:

$$AIC_c = -2\log\mathcal{L} + 2K\frac{N}{N-K-1}$$

where K is the number of independent parameters of the fitting model and equal to 4 and 6 for SSM$_{vas}$ and SSM$_{full}$, respectively, N is the number of measurement points in DCE-MRI data, and log L is the maximum logarithmic likelihood probability.

(6-3) Calculate the corrected Akaike Information Criterion score difference between the two models, $\Delta AIC_c = AIC_c$(SSM$_{full}$)−AIC$_c$(SSM$_{vas}$).

(6-4) Judge whether $\Delta AIC_c$ is no more than −10.

(6-5) when the conditions in step (6-4) are satisfied, it means that the pixel is more suitable for SSM$_{full}$. The fitting parameter results $p_b$, $p_o$, K$^{trans}$, $k_{io}$, $k_{bo}$ obtained by SSM$_{full}$ are assigned to the final $p_b$, $p_o$, K$^{trans}$, $k_{io}$, $k_{bo}$. When the conditions in step (6-4) are not met, it means that the pixel is more suitable for SSM$_{vas}$. The fitting parameter results $p_b$, K$^{trans}$, $k_{bo}$ obtained by SSM$_{vas}$ are assigned to the final $p_b$, K$^{trans}$, $k_{bo}$. In the process of SSM$_{vas}$, $p_o$ and $k_{io}$ are not fitting parameters and fixed, so they have no fitting values and are set as invalid values (NaN).

Figure 7:
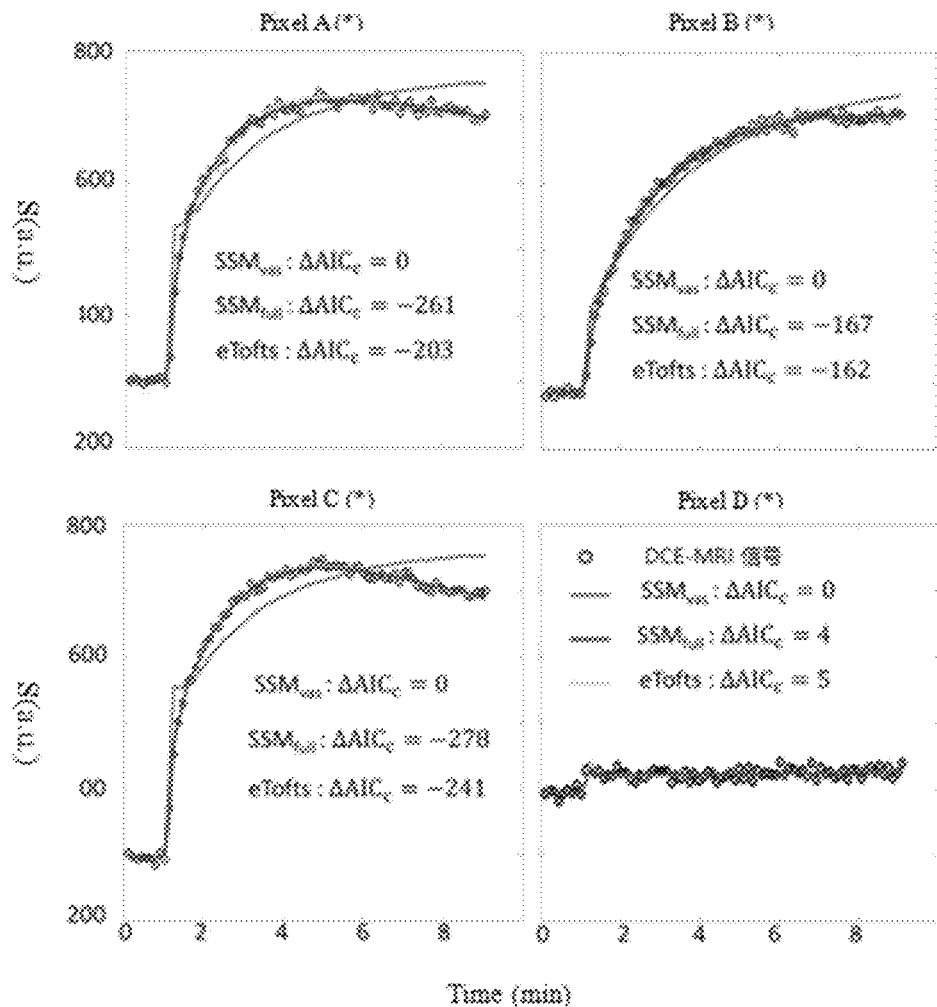
FIG. 7 shows the typical DCE-MRI time-series curve (open circles) and model fitting performance.
Figure 8:
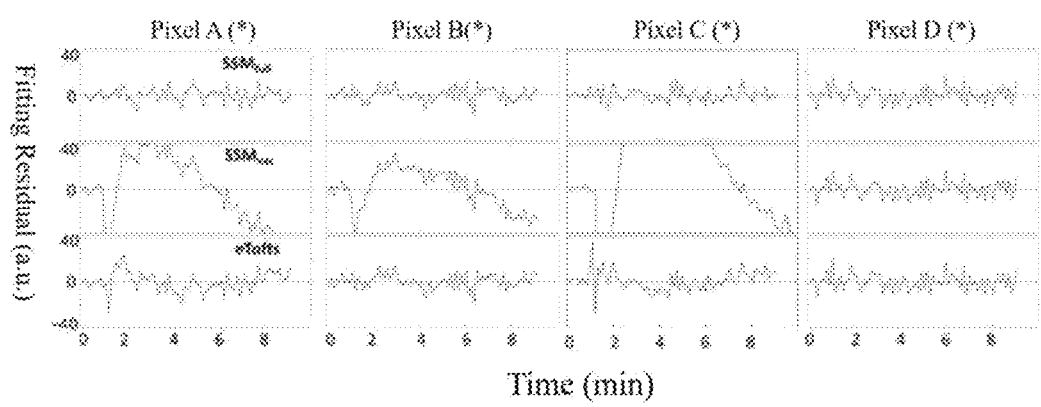
FIG. 8 shows the fitting residuals of different models in FIG. 7.

FIGS. 6-8 show an example of step 6. Among them, (A) in FIG. 6 shows axial, 1.5 mm slice thickness DCE-MR images before CA injection, 1.5 minutes after CA injection and 9 minutes after CA injection (from left to right), in which the left and right arrows point to the recurrent tumor and radiation necrosis area, respectively. Enlarged images of the area surrounded by box (A, middle) are shown in FIG. 6B, including T1 image with skull removed, DCE-MRI image at 1.5 min after CA injection, and AIC difference distribution map with $\Delta AIC_c = AIC_c$(SSM$_{full}$ I)−AIC$_c$ (SSM$_{vas}$). According to the AIC$_c$ analysis, most of the pixels located in the tumor region showed obvious SSM$_{full}$ preference (the AIC$_c$ score of SSM$_{full}$ model is much lower than that of SSM$_{vas}$, $\Delta AIC_c$<−10), while nearly normal tissues preferred SSM$_{vas}$ model.

FIG. 7 shows the typical DCE-MRI time-series curve (open circles) and model fitting performance. Four pixels are selected, and A-C and D are from tumor and normal tissue, respectively. The positions of the representative pixels are shown with asterisks in FIG. 6B (middle). Different grayscale curves show the fitting results of SSM$_{vas}$, SSM$_{full}$ and classical model—extended Tofts (eTofts) model. $\Delta AIC_c$ in each panel is marked as the difference of $AIC_c$ between the corresponding model and the $SSM_{vas}$. FIG. 8 shows the fitting residuals of different models in FIG. 7.

FIG. 7 and FIG. 8 show that $SSM_{vas}$ can't fit DCE-MRI time-series curve well in tumor region, while $SSM_{full}$ can fit DCE-MRI time-series curves better without obvious abnormal fitting residual points. In normal tissues, $SSM_{vas}$ and $SSM_{full}$ can both fit the DCE-MRI time-series curve of the selected pixels well, but the $AIC_c$ score of $SSM_{full}$ is higher than that of $SSM_{vas}$, which suggests that the $SSM_{full}$ with more fitting parameters over fits the signal, and $SSM_{vas}$ is enough to fit the curve.

7. As shown in FIG. 4, the error analysis of $k_{io}$ and $k_{bo}$ in step 6 is carried out, and only pixel results with 95% confidence interval localized in $[0\ s^{-1}\ 20\ s^{-1}]$ or the lower limit of 95% confidence interval bigger than $5\ s^{-1}$ are retained to generate the final distribution maps of $k_{io}$, $k_{bo}$, along with the distribution maps of $K^{trans}$, $p_b$, $p_o$.

(7-1) When the optimal model is $SSM_{full}$, the specific process of $k_{bo}$ (or $k_{io}$) error analysis is as follows:

(7-1-1) Determine the 95% confidence interval of $k_{bo}$ (or $k_{io}$) by fixed $k_{bo}$ (or $k_{io}$) value, fitting all the remaining parameters of $SSM_{full}$ by the nonlinear least square algorithm, and then changing the value of $k_{bo}$ (or $k_{io}$) in the interval of $[0\ s^{-1}\ 20\ s^{-1}]$ in small steps, and repeat the fitting processes until:

$$\chi^2 \geq \chi_0^2 \left[1 + \frac{K}{N-K} F(K, N-K, 0.95)\right]$$

Among them, $\chi^2$ is the reduced chi-squared value from the fitting with the $k_{bo}$ or $k_{io}$ fixed at a certain value, $\chi_0^2$ is the reduced chi-squared value with all parameters optimized, F is the F distribution function, K is the number of independent parameters in the fitting model, and N is the number of measurement points in the DCE-MRI data.

(7-1-2) If the 95% confidence interval of $k_{bo}$ or $k_{io}$ is in the interval of $[0\ s^{-1}\ 20\ s^{-1}]$ or the lower limit of 95% confidence interval is bigger than $5\ s^{-1}$, the fitted $k_{bo}$ or $k_{io}$ are retained. When this requirement cannot be met, $k_{bo}$ or $k_{io}$=NaN.

Figure 9:
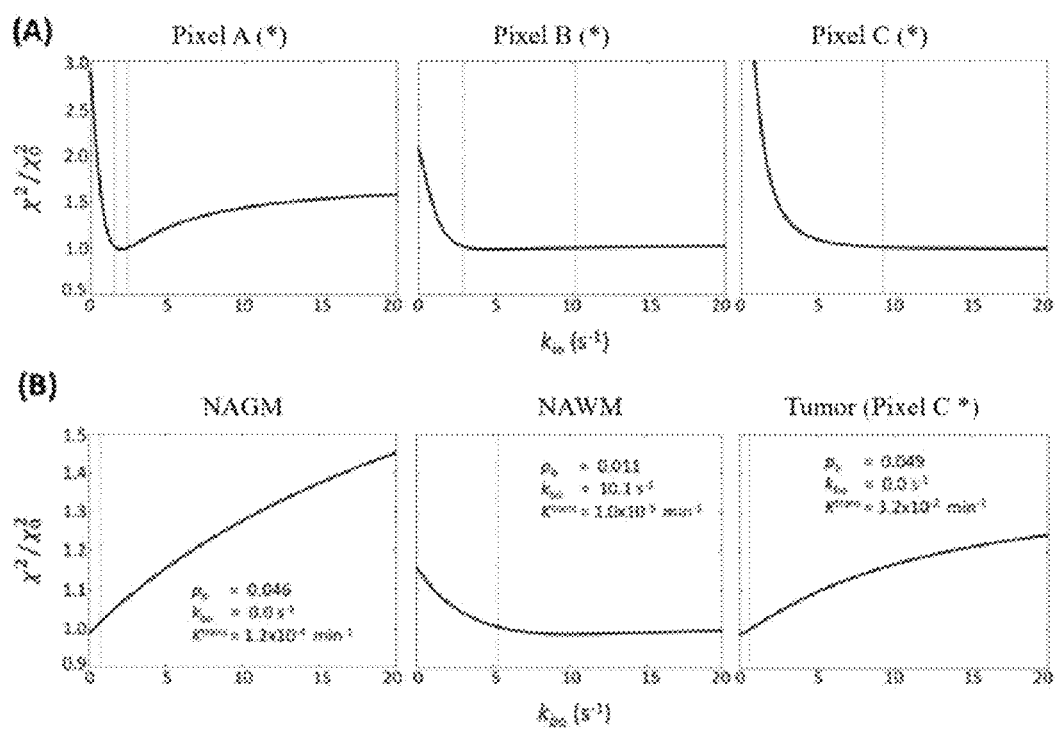
FIG. 9 shows the error analysis results.

The (A) in FIG. 9 performed the error analysis on $k_{io}$ for the tumor pixels A-C in FIG. 7 (when the cellular water efflux rate constant $k_{io}$ is set to the fixed value of the transformation, the reduced chi-squared curve of the data of pixels A-C in FIG. 7). The dashed vertical lines represent the 95% confidence level. Pixel A displays a well-defined error range. And Pixel B displays a wider but still determined error range. In Pixel C, the significant lower error bound can be determined. All three cases are acceptable error range.

(7-2) When the optimal model is $SSM_{vas}$, the specific process of $k_{bo}$ error analysis is as follows:

(7-2-1) Determine the 95% confidence interval of $k_{bo}$ by fixed $k_{bo}$ value, fitting all the remaining parameters of $SSM_{vas}$ by the nonlinear least square algorithm, and then changing the value of $k_{bo}$ in the interval of $[0\ s^{-1}\ 20\ s^{-1}]$ in small steps, and repeat the fitting processes until:

$$\chi^2 \geq \chi_0^2 \left[1 + \frac{K}{N-K} F(K, N-K, 0.95)\right]$$

Among them, $\chi^2$ is the reduced chi-squared value from the fitting with the $k_{bo}$ fixed at a certain value, $\chi_0^2$ is the reduced chi-squared value with all parameters optimized, F is the F distribution function, K is the number of independent parameters in the fitting model, and N is the number of measurement points in the DCE-MRI data.

(7-2-2) If the 95% confidence interval of $k_{bo}$ is in the interval of $[0\ s^{-1}\ 20\ s^{-1}]$ or the lower limit of 95% confidence interval is bigger than $5\ s^{-1}$, the fitted $k_{bo}$ are retained. When this requirement cannot be met, $k_{bo}$=NaN.

The (B) in FIG. 9 performed the error analysis on $k_{bo}$ for the typic normal gray matter (GM) pixel, normal white matter (WM) pixel, and Pixel C located in tumor in FIG. 8 (when the vascular water efflux rate constant $k_{bo}$ is set to the fixed value of the transformation, the reduced chi-squared curve of the data of the three pixels). The dashed vertical lines represent the 95% confidence level. GM pixel and Pixel C displays a well-defined error range (well-determined upper error boundary and the lower error boundary is $0\ s^{-1}$). In WM pixel, only the lower error bound can be determined. All three cases are acceptable error range.

Through the above steps 1-7, $p_b$, $p_o$, $K^{trans}$, $k_{io}$, $k_{bo}$ distribution maps can be generated.

Figure 10:
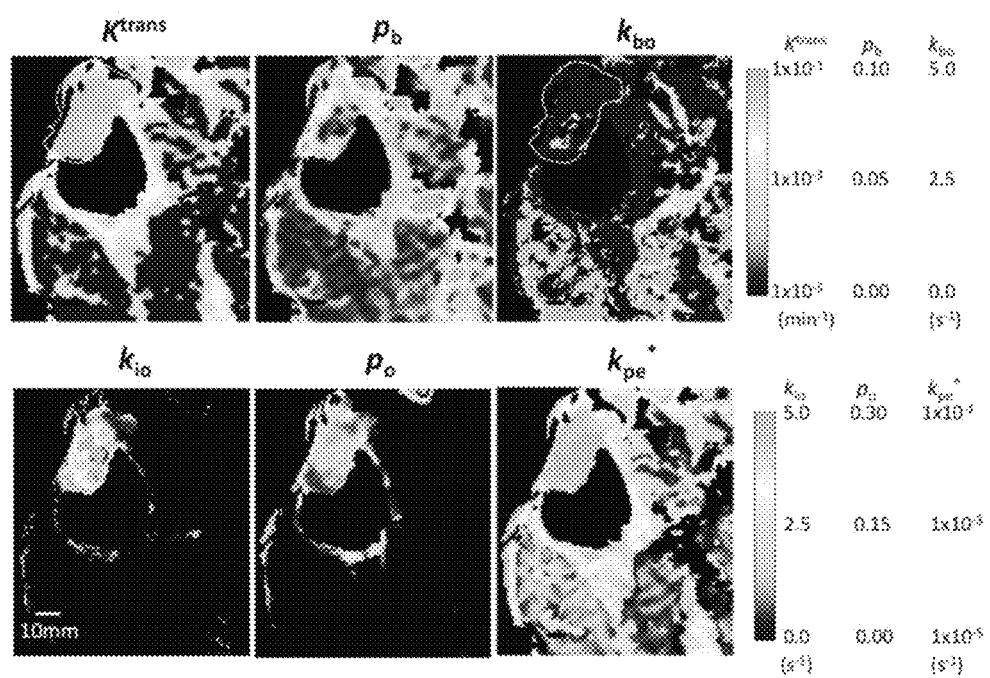
FIG. 10 shows the SSM parametric maps of the images in FIG. 6.

In the present invention, the analysis results of this method are shown in FIG. 10, which are parametric maps corresponding to the enlarged area in FIG. 6, including $K^{trans}$, $p_b$, $k_{bo}$, $k_{io}$, $p_o$ and $k_{pe}^*$ ($=2.2\ K^{trans}/p_b$). This method only analyzes pixels with T1<3500 ms. In these parametric maps, only the pixels with $\Delta AIC_c$ no more than $-10$ are analyzed by $SSM_{full}$, and the following parameters are generated: $K^{trans}$, $p_b$, $k_{bo}$, $k_{io}$, $p_o$ and its derivative $k_{pe}^*$ ($=2.2\ K^{trans}/p_b$). All other pixel data are analyzed by $SSM_{vas}$ and the following parameter are displayed: $K^{trans}$, $p_b$, $k_{bo}$, $k_{pe}^*$. In the final $k_{bo}$ (or $k_{io}$) map, only the following pixels are included: the upper and lower boundaries of the 95% confidence interval of $k_{bo}$ (or $k_{io}$) of this pixel are between 0-20 $s^{-1}$ or the lower boundary is bigger than $5\ s^{-1}$.

Tumor tissues show obvious enhancement of $K^{trans}$, $p_b$ and $k_{pe}^*$, which was in line with expectations. A large number of references show that there are vascular hyperplasia and enhanced vascular permeability in tumors. However, there is an obvious heterogeneity of $k_{io}$ distribution in tumors, which may represent the distribution of tumor subcells with different metabolic levels and pathology. The tumor shows a rapid decrease of $k_{bo}$, which may indicate that the active transmembrane water molecule exchange of vascular is stopped in the tumor.

The invention claimed is:

1. An analysis method for dynamic contrast-enhanced magnetic resonance images (DCE-MRI), which is characterized by the analysis steps described below:

(1) obtaining the biological individual's vascular contrast agent concentration as a function of time from the time-series DCE-MRI data;

(2) according to the time-series signal of vascular contrast agent concentration in step (1), fitting the DCE-MRI time-series signal of each pixel by the nonlinear least sum of square algorithm using the Full Shutter-Speed model ($SSM_{full}$) and the Simplified Shutter-Speed model ($SSM_{vas}$) respectively, and obtaining the DCE-MRI signal fitting results of $SSM_{full}$ model and $SSM_{vas}$ model of each pixel;

(3) using corrected Akaike information criterion ($AIC_c$) to score and compare the DCE-MRI signal fitting results of the $SSM_{full}$ model and the $SSM_{vas}$ model in each pixel, according to the score from the corrected Akaike information criterion evaluating the $SSM_{full}$ model and the $SSM_{vas}$ model in each pixel, selecting the optimal model from the $SSM_{full}$ model and the $SSM_{vas}$ model for each pixel;

(4) carrying out fitting according to the optimal model selected in step (3); if the optimal model being SSM$_{full}$ model, producing distribution maps of five groups of physiological parameters produced after fitting; the five groups of physiological parameters being the contrast agent (CA) volume transfer constant between blood plasma and extravascular-extracellular space (K$^{trans}$), intravascular water mole fraction (p$_b$), extravascular-extracellular water mole fraction (p$_o$), the vascular water efflux rate constant (k$_{bo}$) and the cellular water efflux rate constant (k$_{io}$); if the optimal model being SSM$_{vas}$ model, due to p$_o$ and k$_{io}$ not being considered as estimated parameters, obtaining only distribution maps of three groups of physiological parameters after fitting; the three groups of physiological parameters being K$^{trans}$, p$_b$ and k$_{bo}$;

(5) performing error analysis on the k$_{io}$ and k$_{bo}$ obtained in step (4) and only reserving the pixel results with 95% confidence interval in the range of [0s$^{-1}$ 20s$^{-1}$] or the lower limit of 95% confidence interval greater than 5 s$^{-1}$, resulting the final k$_{io}$ and k$_{bo}$ parametric distribution maps and the K$^{trans}$, p$_b$, p$_o$ parametric distribution map.

2. The dynamic contrast-enhanced magnetic resonance image (DCE-MRI) analysis method of claim 1, wherein the basic assumption of SSM$_{full}$ model in Step (2) is that water molecules are in three compartments of the vascular space, extravascular-extracellular space and intracellular space and water exchange happens between vascular and extravascular-extracellular spaces and between extravascular-extracellular and intracellular spaces and no water exchange happens between vascular and intracellular spaces.

3. The dynamic contrast-enhanced magnetic resonance images (DCE-MRI) analysis method of claim 2, wherein the SSM$_{full}$ model's fitting parameters are K$^{trans}$, p$_b$, p$_o$, k$_{bo}$ and k$_{io}$.

4. The dynamic contrast-enhanced magnetic resonance image (DCE-MRI) analysis method of claim 1, wherein the basic assumption of the SSM$_{vas}$ model in step (2) is that water molecules are in three compartments of vascular space, extravascular-extracellular space and intracellular space and water exchange processes happen between vascular and extravascular-extracellular spaces and there is no water exchange process between vascular and intracellular space, wherein the SSM$_{vas}$ model ignores the effect on the magnetic resonance signal induced by the water exchange process between extravascular-extracellular space and intracellular space and the intercellular water molar fraction.

5. The dynamic contrast-enhanced magnetic resonance image analysis method of claim 4, wherein the SSM$_{vas}$ model includes three fitting parameters are K$^{trans}$, p$_b$ and k$_{bo}$, and p$_o$ and k$_{io}$ are fixed at 0.2 and 1000 s$^{-1}$, respectively.

6. The dynamic contrast-enhanced magnetic resonance image analysis method of claim 1, wherein in step (3), if the difference between the corrected Akaike information criterion scores of the SSM$_{full}$ model and the corrected Akaike information criterion (AIC$_c$) score of the SSM$_{vas}$ model of a pixel is no more than −10, the optimal model is the SSM$_{full}$ model for this pixel; if the difference between the corrected Akaike information criterion score of the SSM$_{full}$ model and the corrected Akaike information criterion (AIC$_c$) score of the SSM$_{vas}$ model of a pixel is more than −10, then the optimal model is the SSM$_{vas}$ model for this pixel.

7. The analysis method of dynamic contrast-enhanced magnetic resonance image of claim 6, wherein the corrected Akaike information criterion (AIC$_c$) score is calculated as follows:

$$AIC_c = -2\log L + 2K\frac{N}{N-K-1}$$

wherein K is the number of the estimated model parameters, and K=4 for SSM$_{vas}$ model and K=6 for SSM$_{full}$ model, N is the number of measurements in DCE-MRI, and log L is the maximized log likelihood.

8. The analysis method of dynamic contrast-enhanced magnetic resonance image of claim 1, wherein in step (5), the 95% confidence interval of k$_{bo}$ or k$_{io}$ in the error analysis is determined by fixing the k$_{bo}$ (or k$_{io}$) value, and then fitting all the remaining parameters via the nonlinear least sum of square method, and then changing the k$_{bo}$ or k$_{io}$ value in the [0 s$^{-1}$ 20 s$^{-1}$] interval in small step size and repeating the fitting until:

$$\chi^2 \geq \chi_0^2\left[1 + \frac{K}{N-K}F(K, N-K, 0.95)\right]$$

wherein $\chi^2$ is the reduced chi-squared value from the fitting with the parameter of k$_{bo}$ or k$_{io}$, $\chi_0^2$ is the reduced chi-squared value with all parameters optimized, and F is the F distribution function, K is the number of the estimated model parameters, N is the number of measurements in the DCE-MRI signal.

* * * * *